United States Patent [19]
Arai

[11] Patent Number: 4,547,687
[45] Date of Patent: Oct. 15, 1985

[54] MICROMOTOR WITH BUILT-IN COOLING MEDIUM PIPES

[75] Inventor: Eiichi Arai, Kyoto, Japan

[73] Assignee: Kabushiki Kaisha Morita Seisakusho, Kyoto, Japan

[21] Appl. No.: 674,472

[22] Filed: Nov. 21, 1984

Related U.S. Application Data

[63] Continuation of Ser. No. 429,118, Sep. 30, 1982.

[30] Foreign Application Priority Data

Oct. 12, 1981 [JP] Japan ............................ 56-151108[U]

[51] Int. Cl.[4] ............................................. H02K 9/00
[52] U.S. Cl. ............................... 310/58; 310/40 MM; 310/154
[58] Field of Search ................. 310/40 MM, 154, 254, 310/258, 47, 50, 52, 54, 58, 60 R, 60 A, 64, 65, 59; 433/84, 104, 131

[56] References Cited

U.S. PATENT DOCUMENTS 2,513,227  6/1950  Wylie ................................... 310/154
3,213,303  10/1965  Riley ..................................... 310/50
4,007,529  2/1977  Fleer .................................... 433/131
4,039,871  8/1977  Yamashita ........................... 310/154
4,184,256  1/1980  Loge .................................... 433/104
4,237,393  12/1980  Landgraf ............................. 310/154
4,279,596  7/1981  Weber .................................. 433/131

FOREIGN PATENT DOCUMENTS 2431472  1/1976  Fed. Rep. of Germany ...... 433/131

Primary Examiner—R. Skuddy
Attorney, Agent, or Firm—Koda and Androlia

[57] ABSTRACT

This disclosure relates to a small-sized, high-power micromotor with built-in cooling medium pipes for medical treatment. The motor which is structurally of the type wherein the stator of the motor includes a permanent magnet and a magnetic yoke encircling the magnet is improved in that the cooling medium pipes are incorporated into the motor by providing at least one cooling medium pipe receptor portion in the magnetic poles of the yoke or in the vicinity of the yoke without reducing motor performance nor increasing the diameter of the motor.

1 Claim, 5 Drawing Figures

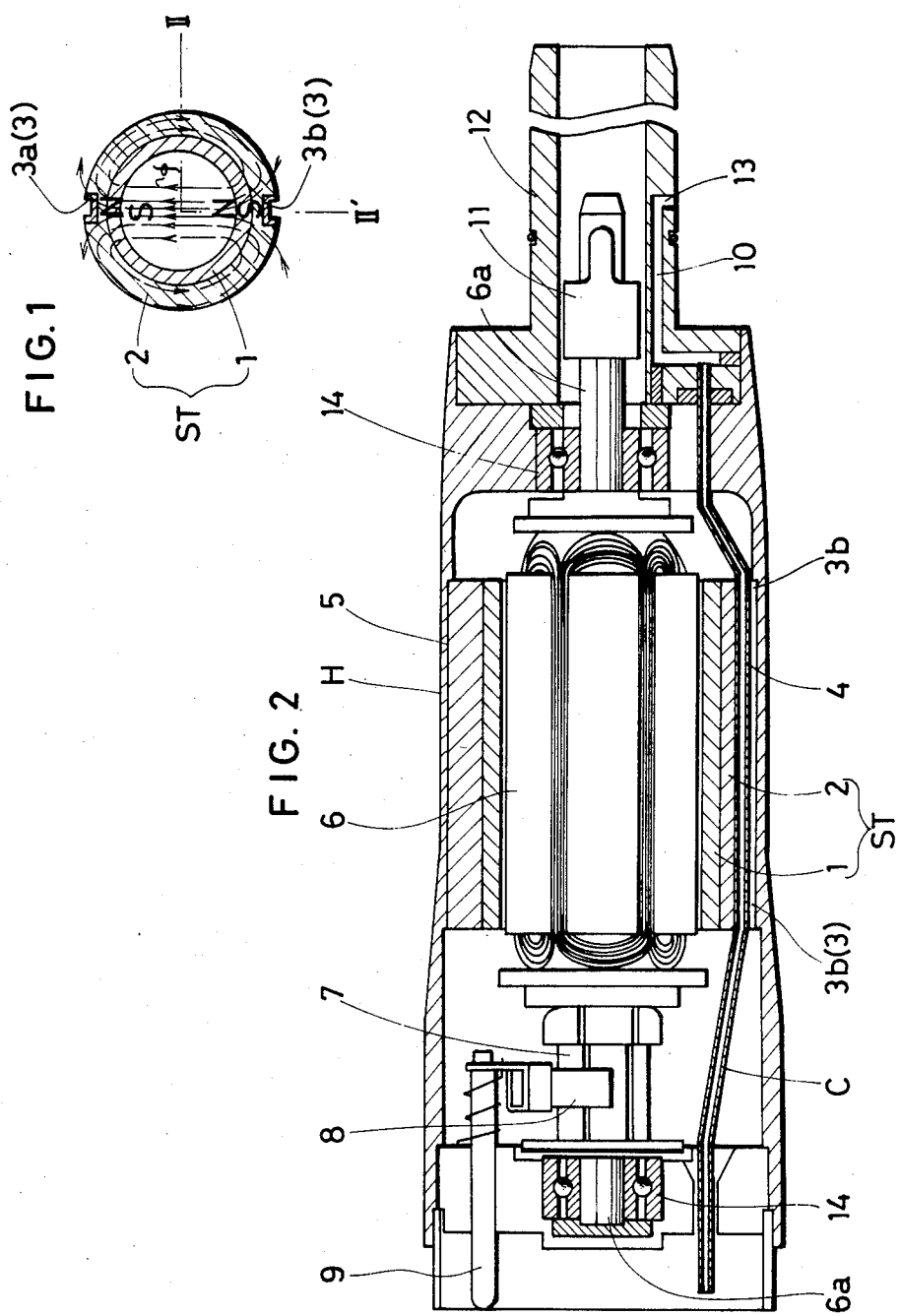

MICROMOTOR WITH BUILT-IN COOLING MEDIUM PIPES

This is a continuation of application Ser. No. 429,118, filed Sept. 30, 1982.

BACKGROUND OF THE INVENTION

1. Field of the Invention

This invention relates generally to a micromotor with built-in cooling medium pipes and more particularly to improvements in a small-size, high power micromotor used in a dental handpiece and other medical appliances of the type wherein a stator of the micromotor structurally contains a permanent magnet and a magnetic yoke encircling the outer circumference of the permanent magnet.

2. Prior Art

In a dental handpiece, for example, a pipe for feeding a cooling medium (mainly water) for preventing heat generated during tooth cutting is used in combination with a handpiece and a supply of water during tooth cutting from the front end of the pipe to a point of the region to be cut is a minimum requirement. Heretofore, handpieces have been classified into a type having such a cooling medium pipe mounted outside thereof and a type including the pipe inside thereof Recently, in order to improve the cutting property of a handpiece, various attempts have been made to improve also the micromotor used in the handpiece. For example, the material used in the micromotor has been changed from a conventional alnicoic material to a material of high energy density, such as rare earth cobaltic material. In this case, a stator not made of alnicoic material but a stator having outer cicumference of a permanent magnet made of rare earth cobaltic material and encircled with a yoke has been proposed so as to further strengthen the effective magnetic flux and to promote miniaturization of a motor. The device of the invention relates to a structure of such a type of micromotor which makes it possible to incorporate a micromotor cooling medium pipe in the micromotor without changing the performance of the motor nor increasing the size of the motor. A description will be given below of a structure of a conventional dental micromotor having a cooling medium pipe therein and of the disadvantages of the structure.

(i) A nonmagnetic body portion encircling a stator is disposed between a motor housing and the stator; and an area for containing the cooling medium pipe therein is provided in a nonmagnetic body portion.

(ii) Two pieces of permanent magnet made of alnicoic material and shaped arcuate in section are disposed in opposed relation and two yokes corresponding to a sector area between two magnet pieces are interposed between such two magnet pieces so as to form a cylindrical stator as a whole and a pipe for a cooling medium is disposed substantially in the middle of the yokes.

The structure thus obtained prevents the pipe from producing an adverse effect on effective magnetic flux and accordingly, the structure offers the advantage that the motor need not be increased in size. However, the structure above cannot be applied to a motor in which are used a magnet of rare earth cobaltic material that has recently come to be used instead of alnicoic material and a yoke encircling the outer cicumference of the magnet.

SUMMARY OF THE INVENTION

This invention has an object to provide a micromotor having cooling medium pipes built therein and being free from the disadvantages described above.

The object is achieved by providing at least one cooling medium pipe receptor portion in the magnetic poles of a yoke or in the vicinity of the yoke without reducing motor performance nor increasing the diameter of the motor. This invention will now be described in detail with reference to the accompanying drawings illustrating preferred embodiments of the invention.

BRIEF DESCRIPTION OF THE DRAWINGS

The above-mentioned features and objects of the present invention will become more apparent with reference to the following description taken in conjunction with the accompanying drawings, wherein like reference numerals denote like elements, and in which:

FIG. 1 is a sectional front view showing one embodiment of a stator forming the essential part of the micromotor of this invention;

FIG. 2 is a sectional view of the essential part taken along the line II—II' of FIG. 1 and shows a stator and substantially the whole of the stator contained in a dental handpiece in section.

DETAILED DESCRIPTION OF THE INVENTION

This invention relates to a micromotor used in medical treatment wherein the micromotor includes a stator ST. The stator ST includes a cylindrical permanent magnet diametrically magnetized or substantially arcuate pieces 1a and 1b diametrically magnetized and having the same radius of curvature and arc and disposed in opposed relation with each other to form a substantially cylindrical magnet 1. The stator ST further includes a yoke 2 encircling the whole of the outer circumference of the permanent magnet 1 being in contact therewith. The micromotor used in medical treatment is characterized in that it includes a receptor portion 3 for at least one cooling medium pipe C in the magnetic poles S, N of the yoke 2 or in the vicinity of the poles S and N.

The permanent magnet 1 shown is made of rare earth cobaltic material and the yoke 2 is made of soft magnetic material. In the embodiments shown in FIGS. 1, 2 and 3, the magnet 1 is cylindrical in shape. In the embodiments shown in FIGS. 4 and 5, the magnet 1 maintains a substantially cylindrical relation by the arcuate pieces 1a and 1b having the same radius of curvature and arc and being disposed in opposed relation with each other to form a substantially cylindrical permanent magnet 1.

Figure 3:
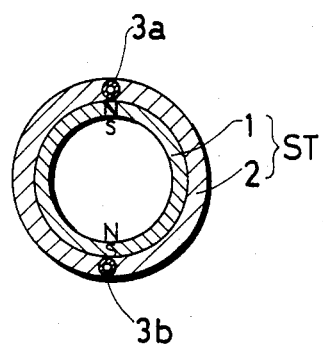
FIGS. 3, 4 and 5 are respectively longitudinal sectional front views showing different embodiments of a stator of this invention.
Figure 4:
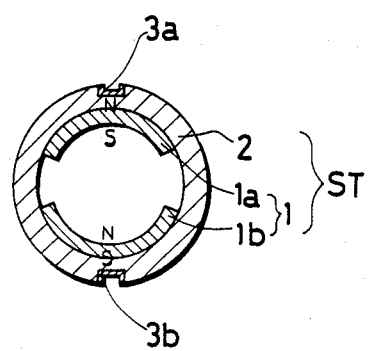
Figure 5:
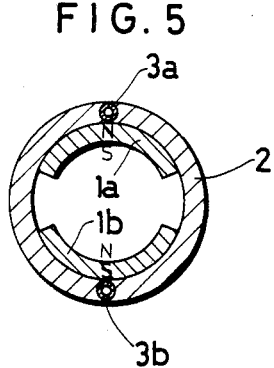

The yoke 2 in any of the embodiments encircles the whole of the outer circumference of the magnet 1 in contact with the yoke 2. The yoke 2 also includes receptor portions 3a and 3b for two cooling medium pipes C in opposed relation with each other in the magnetic poles S and N of the yoke 2 or in the vicinity thereof; namely, on the diametrical line of the permanent magnet 1. The receptor poritons 3a and 3b shown in FIGS. 1 and 4 are provided in the form of notched grooves formed on the outer circumference of the yoke 2 along the longitudinal direction thereof, while the receptor portions 3a and 3b shown in FIGS. 3 and 5 are provided in the form of bores extending through the thickness of the yoke 2 along the longitudinal direction thereof.

The internal structure of the handpiece containing the stator ST of FIG. 1 is shown in FIG. 2. In FIG. 2, there is disposed a rotor 6 inside of the stator ST constructed of the permanent magnet 1 and yoke 2 and shafts 6a in the front and rear of the rotor 6 are journalled in bearings 14. Supply of power to a plug 9 exposed in the rear of a handpiece body H energizes the rotor 6 through a brush 8 and a rectifier 7 to rotate the rotor 6. To the front portion of the handpiece body H is fixed a sleeve 12. To the sleeve 12 is replaceably connected a straight handpiece or a contra handpiece. In such connection of the handpiece, a clutch 11 is connected to another clutch (not shown) built into the handpiece to transmit the power of the rotor 6 to the clutch 11. The cooling medium pipes C are disposed inside of the recessed portions 3a and 3b (only 3b is shown in FIG. 2) extend longitudinally from the rear portion to the front portion of the handpiece body H and are connected to the cooling medium passages (bores) 10 formed inside of the sleeve 12 in the front portion. The front ends of the passageways 10 terminate at outlets 13. Such being the structure, the cooling medium is supplied from the outlets 13 of the passageways 10 through the pipes C to an intended point of area.

As shown, the embodiments of this invention because they incorporate the cooling medium pipes C in the motor by positioning the receptor portions 3a and 3b in the magnetic poles N and S of the yoke 2 or in the vicinity of the poles N and S, the effective magnetic flux $\phi$ of the magnet 1 is not reduced in spite of the presence of the receptor portions 3a and 3b and pipes C. As shown in broken lines in FIG. 1 since the effective magnetic flux $\phi$ passes through the yoke 2 in the same manner as in the case wherein no receptor portions 3a and 3b are provided, there is no possibility of motor performance deterioration. From this fact, this invention makes it possible for the motor to obtain such an advantage as to incorporate cooling medium pipes therein without reducing motor performance.

The description above is given of the embodiments of this invention wherein the receptor portions 3 are disposed in pairs and in symmetrical relation on the diametrical line of the yoke 2 so as to dispose two pipes C in opposed relation with each other. This is intended to make desirable equal distribution of magnetic flux in a motor and is not intended to exclude the case wherein there is provided one receptor portion 3; namely, one pipe C. However, the symmetrical arrangement of the internal magnetic flux is expected to be technically desirable and for this reason, the use of at least a pair of receptor portions 3a and 3b is preferred. Also, the embodiment wherein the recessed grooves 3a and 3b are provided in the form of notched grooves is considered the best mode of the invention not only in that the embodiment provides less possibility of crossing (reducing) magnetic flux $\phi$ than the embodiment wherein the grooves are substituted by bores but also in that the embodiment is favorable in view of machining.

I claim:

1. A micromotor with built-in cooling medium pipes provided in a handpiece body comprising:
    a stator of said micromotor comprising a cylindrical permanent rare earth cobalt magnet diametrically magnitized;
    a yoke of a soft magnetic material encircling the whole of the outer periphery of said cylindrical rare earth cobalt permanent magnet and being in contact therewith;
    said micromotor being characterized in that the micromotor comprises a pair of receptor portions in the form of notched grooves disposed in the outer circumference of said yoke in opposed relationship with each other on the diametrical line of said permanent magnet, each of said pair of receptor portions being provided adjacent a magnetic pole of said permanent magnet and at least one of said cooling medium pipes extending through at least one of said receptor portions.

* * * * *